(12) United States Patent
Rainis et al.

(10) Patent No.: US 6,759,438 B2
(45) Date of Patent: Jul. 6, 2004

(54) USE OF OXYGEN ANALYSIS BY GC-AED FOR CONTROL OF FISCHER-TROPSCH PROCESS AND PRODUCT BLENDING

(75) Inventors: Andrew Rainis, Walnut Creek, CA (US); D J O'Rear, Petaluma, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 129 days.

(21) Appl. No.: 10/047,015

(22) Filed: Jan. 15, 2002

(65) Prior Publication Data

US 2003/0153634 A1 Aug. 14, 2003

(51) Int. Cl.[7] .................... C07C 27/00; C10G 25/00; C10G 65/00; C10G 17/00; C10G 17/04; C10G 5/00; C10M 175/00; G01N 30/02; G01N 31/00

(52) U.S. Cl. .................... 518/700; 208/27; 208/59; 208/93; 208/177; 208/184; 208/311; 208/341; 436/161; 702/25; 702/30

(58) Field of Search .................... 208/27, 59, 177, 208/184, 311, 341, 93; 518/700; 702/25, 30; 436/161

(56) References Cited

U.S. PATENT DOCUMENTS

| | | |
|---|---|---|
| 4,044,063 A | 8/1977 | Ireland et al. |
| 4,059,648 A | 11/1977 | Derr et al. |
| 4,071,574 A | 1/1978 | Milstein et al. |
| 4,293,220 A | 10/1981 | Denton et al. |
| 4,507,517 A | 3/1985 | Devries et al. |
| 4,568,663 A | 2/1986 | Mauldin |
| 4,599,474 A | 7/1986 | Devries et al. |
| 4,704,487 A | 11/1987 | Devries et al. |
| 4,704,493 A | 11/1987 | Devries et al. |
| 4,709,108 A | 11/1987 | Devries et al. |
| 4,734,537 A | 3/1988 | Devries et al. |
| 4,814,533 A | 3/1989 | Devries et al. |
| 4,814,534 A | 3/1989 | Devries et al. |
| 4,814,538 A | 3/1989 | Devries et al. |
| 4,832,819 A | 5/1989 | Hamner |
| 5,151,371 A | 9/1992 | Quimby et al. |
| 5,324,335 A | 6/1994 | Benham et al. |
| 5,500,449 A | 3/1996 | Benham et al. |
| 5,504,118 A | 4/1996 | Benham et al. |
| 5,506,272 A | 4/1996 | Benham et al. |
| 5,543,437 A | 8/1996 | Benham et al. |
| 5,600,134 A | 2/1997 | Ashe et al. |
| 5,620,670 A | 4/1997 | Benham et al. |
| 5,621,155 A | 4/1997 | Benham et al. |
| 5,645,613 A | 7/1997 | Benham et al. |
| 5,766,274 A | 6/1998 | Wittenbrink et al. |
| 5,807,413 A | 9/1998 | Wittenbrink et al. |
| 5,895,506 A | 4/1999 | Cook et al. |
| 5,985,135 A | 11/1999 | Gupta |
| 6,274,029 B1 * | 8/2001 | Wittenbrink et al. ......... 208/15 |
| 6,275,775 B1 | 8/2001 | Baco et al. |

FOREIGN PATENT DOCUMENTS

| | | |
|---|---|---|
| EP | 0609079 A1 | 8/1994 |
| EP | 0921184 A1 | 6/1999 |
| FR | 2772783 A1 | 12/1997 |
| FR | 2772784 A1 | 3/1998 |

OTHER PUBLICATIONS

Kaiser, M.A, *Chromatography, Kirk Kirk–Othmer: Encyclopedia Chemical Technology, Chlorocarbons and Chlorohydrocarbons–$C_2$, to Combustion Technology*, vol. 6, 4th Edition, 1993, pp. 207–228, Wiley–Interscience Publication, John Wiley & Sons, New York.

Quimby, B.D., et al., *Improved Measurement of Sulfur and Nitrogen Compounds in Refinery Liquids Using Gas Chromatography–Atomic Emission Detection, Journal of Chromatographic Science*, vol. 36, No. 9, Sep. 1998. pp. 435–443. Preston Publications: Division of Preston Industries, Niles, Illinois.

Quimby, B.D., et al., *Improved Analysis of Sulfur, Nitrogen, and Other Heteroatomic Compounds in Gasoline–and Diesel–Range Materials Using GC/Atomic Emission Detection, Hewlett Packard: Application Note 228–394, Gas Chromatography*, Dec. 1997, pp. 1–11, Hewlett Packard, USA.

"Sensitive and Selective Universal Element Detection for Routine or Research Analyses," Hewlett Packard Brochure, HP G2350A AED: For Versatile, Highly Sensitive and Selective Detection, 1999, U.S.

UK Search Report for GB 0300082.5 dated Jul. 10, 2003.

* cited by examiner

Primary Examiner—J. Parsa
(74) Attorney, Agent, or Firm—Burns, Doane, Swecker & Mathis, L.L.P.

(57) ABSTRACT

Methods for producing a substantially paraffinic Fischer-Tropsch product or a blended Fischer Tropsch product comprising a selected oxygenate concentration, and if required, a selected oxygenate concentration of specific individual oxygenates, are disclosed. The methods of the present invention measure oxygenate concentration using GC-AED. The oxygenate measurements obtained using the GC-AED may be used to adjust and control various processes used to produce, upgrade, or finish Fischer Tropsch products to provide Fischer Tropsch products with a selected oxygenate concentration, and if required, a selected oxygenate concentration of specific individual oxygenates.

37 Claims, 2 Drawing Sheets

USE OF OXYGEN ANALYSIS BY GC-AED FOR CONTROL OF FISCHER-TROPSCH PROCESS AND PRODUCT BLENDING

The present invention relates to an improved process for producing Fischer Tropsch products through measuring oxygenate concentration using GC-AED.

BACKGROUND OF THE INVENTION

The concentration of total oxygenates in Fischer-Tropsch products often needs to be maintained within established limits for optimal product characteristics. In addition, it may also be necessary to maintain the concentration of specific individual oxygenates within established limits. Therefore, to achieve the desired concentrations, the concentration of oxygenates, often specific individual oxygenates, in a Fischer-Tropsch product must be measured and controlled. The results from an analysis of oxygenates may be used to regulate operation of the Fischer Tropsch process. Accordingly, accurate measurement of oxygenates and control of their levels to desired set points are needed for efficient production of salable products from Fischer-Tropsch products.

There have been a variety of methods used to measure the concentration of oxygenates in Fischer-Tropsch products, including, elemental analysis, Infrared (IR), simple Gas Chromatography (GC), and GC coupled with mass spectrometry (MS). By way of example, U.S. Pat. No. 5,895,506 to Cook, et al. describes the use of Infrared (IR) techniques to monitor various oxygenate and olefin classes in Fischer-Tropsch products. IR techniques, however, have two disadvantages. First, they require calibration; calibration introduces error because the substance used for calibration may not behave exactly as the compounds in the sample. Second, IR techniques measure only the total concentration of each class of compounds (for example, alcohols, acids, etc.); therefore, they do not provide a distribution by carbon number. In performing and controlling a Fischer Tropsch process, a combined analysis by class and carbon number may be required.

GC may also be used to monitor oxygenate concentration. The basic science of gas chromatography has been known for over a century. GC separates different molecules in a mixture into components with different groups, typically sorted by molecular weight or boiling point. Various detectors can be used with GC. If a majority of the components in the mixture are to be measured, several detectors may be used, including a Thermal Conductivity Detector (TCD) or a Flame-Ionization Detector (FID).

When it is desired to measure a specific minority component in the mixture, it is preferable to use a detector that monitors the family of compounds that encompass the minority component. An example of such a detector is Gas Chromatography coupled with a Mass Spectrometry analyzer (GC-MS,) which can determine the specific components that elute from the GC at the same time. By way of example, U.S. Pat. No. 5,600,134 to Ashe et al. describes a method for controlling the bending of blend stocks using GC-MS. The method of Ashe requires a 10-step process for producing a training set of one or more known properties from reference samples. The training set provides a predicted MS value of the one or more properties against which MS information from the blend stocks may be compared. The training set is used to produce a predicted MS value of the desired properties for blend stocks and blend product samples. While GC-MS may be a good tool for identifying the general nature of compounds in a mixture, it can lack sufficient sensitivity for all operations.

In all of the above listed techniques, when control of specific individual oxygenate compounds at low levels is required, these techniques may be inadequate.

As control and measurement of specific individual oxygenate compounds at low levels may be important to producing salable products from Fischer Tropsch processes, there are needed techniques that can accurately and efficiently measure oxygenates and control their concentrations to selected set points.

SUMMARY OF THE INVENTION

The present invention relates to methods for producing a substantially paraffinic Fischer-Tropsch product or a blended Fischer Tropsch product comprising a selected oxygenate concentration, and if required, a selected oxygenate concentration of specific individual oxygenates. The methods of the present invention measure oxygenate concentration using GC-AED. The oxygenate measurements obtained using the GC-AED may be used to adjust and control various processes used to produce, upgrade, or finish Fischer Tropsch products to provide Fischer Tropsch products with a selected oxygenate concentration, and if required, a selected oxygenate concentration of specific individual oxygenates.

The present invention relates to a method for producing a substantially paraffinic Fischer-Tropsch product comprising at least one oxygenated species. In the method, a concentration of oxygenated species in the substantially paraffinic Fischer-Tropsch product is selected. A carbon number distribution of oxygenated species or a class of oxygenated species may also be selected. A Fischer-Tropsch synthesis is performed to provide a Fischer-Tropsch product stream. A substantially paraffinic product stream containing oxygenated species is isolated from the Fischer-Tropsch product stream. The substantially paraffinic product stream is purified, for example, by hydrotreating, hydrocracking, adsorption, extraction, and combinations thereof, to remove a portion of oxygenated species, to provide a substantially paraffinic Fischer-Tropsch product comprising at least one oxygenated species. The substantially paraffinic Fischer-Tropsch product is monitored for concentration of oxygenated species by GC-AED. The substantially paraffinic Fischer-Tropsch product may also be monitored for carbon number distribution or class of oxygenated species by GC-AED. The conditions of the purification are adjusted to ensure that the concentration of the oxygenated species in the substantially paraffinic Fischer-Tropsch product complies with the selected concentration. The conditions of the purification may also be adjusted to ensure that the carbon number distribution or class of the oxygenated species in the substantially paraffinic Fischer-Tropsch product complies with a selected carbon number distribution or class.

An additional aspect of the present invention relates to a method for producing a substantially paraffinic Fischer-Tropsch product comprising no detectable oxygenated species. In that method, a Fischer-Tropsch synthesis is performed to provide a Fischer-Tropsch product stream. A substantially paraffinic product stream containing oxygenated species is isolated from the Fischer-Tropsch product stream. The substantially paraffinic product stream is purified, for example, by hydrotreating, hydrocracking, adsorption, extraction, and combinations thereof, to remove the oxygenated species, to provide a substantially paraffinic Fischer-Tropsch product comprising no detectable oxygenated species. The substantially paraffinic Fischer-Tropsch product is monitored for concentration of oxygenated species by GC-AED. The conditions of the purification are adjusted to ensure that the concentration of the oxygenated species in the substantially paraffinic Fischer-Tropsch product is not detectable.

The present invention also provides a method for preparing a blended Fischer-Tropsch product comprising at least one oxygenated species. In the method a concentration of oxygenated species in the blended Fischer-Tropsch product is selected. A carbon number distribution of oxygenated species or a class of oxygenated species may also be selected. A Fischer-Tropsch synthesis is performed to provide a Fischer-Tropsch product stream. A substantially paraffinic product stream containing oxygenated species is isolated from the Fischer-Tropsch product stream, for example, by distillation. The substantially paraffinic product stream is blended with at least one non-oxygenate containing hydrocarbon stream to provide a blended product comprising at least one oxygenated species. The blended product is monitored for concentration of oxygenated species by GC-AED. The blended product may also be monitored for carbon number distribution or class of oxygenated species by GC-AED. The blending ratio is adjusted to ensure that the concentration of the oxygenated species in the blended product complies with the selected concentration and carbon number distribution. The blending ratio may also be adjusted to ensure that the carbon number distribution or class of the oxygenated species in the blended product complies with a selected carbon number distribution or class.

The selected concentration of oxygenated species may be between 100 and 5000 wppm (weight parts per million) on a water-free basis. Furthermore, the blended product may be used as diesel fuel or jet fuel. A further step of adding dispersants, detergents, anti-oxidants and ignition improvers to the blended product may also be included.

The at least one non-oxygenate containing hydrocarbon stream may be comprised of a non-oxygenate containing Fischer-Tropsch product stream which is isolated from the Fischer-Tropsch product stream, a conventional petroleum product, or a hydrotreated stream. If the at least one non-oxygenate containing hydrocarbon stream is comprised of a non-oxygenate containing Fischer-Tropsch product stream, the substantially paraffinic product stream may contain alcohol and the blended product may be used as a diesel fuel with reduced emissions. If the at least one non-oxygenate containing hydrocarbon stream is comprised of a hydrotreated stream, the blended product may be a pumpable syncrude.

In a further embodiment of the present invention, the concentration of oxygenated species, carbon number distribution of oxygenated species, class of oxygenated species or combinations thereof may be selected to improve the lubricity of the blended Fischer Tropsch product. Accordingly, the blending ratio of the Fischer Tropsch product stream comprising oxygenated species and the non-oxygenate containing hydrocarbon stream may be adjusted to achieve the improved lubricity.

An additional aspect of the present invention relates to an integrated method for preparing a Fischer-Tropsch product comprising at least one oxygenated species. In the integrated method the substantially paraffinic product stream comprising at least one oxygenated species to be blended with at least one non-oxygenate containing hydrocarbon stream is produced using GC-AED to monitor the concentration of the oxygenated species. A carbon number distribution of oxygenated species or a class of oxygenated species may also be monitored using GC-AED. This substantially paraffinic Fischer-Tropsch product comprising at least one oxygenated species is blended with at least one non-oxygenate containing hydrocarbon stream. This blending is also monitored using GC-AED to ensure that the blended product has a selected concentration of oxygenated species. This blending may also be monitored using GC-AED to ensure that the blended product has a selected carbon number distribution or a class of oxygenated species.

Definitions:

The following terms will be used throughout the specification and will have the following meanings unless otherwise indicated.

"Conventional petroleum product" means any products from a conventional source, i.e. not synthetically produced. Conventional petroleum products include, for example, petroleum, diesel fuel, solvent, jet fuel, naphtha, lube base stock, lube base stock feedstock, and lube base oil.

"Heteroatom" refers to an atom other than carbon or hydrogen such as sulfur, oxygen, nitrogen, and the like.

"Hydrocarbonaceous" means containing hydrogen and carbon atoms and potentially also containing heteroatoms, such as oxygen, sulfur, nitrogen, and the like, as well.

"Hydrocarbonaceous product" means any product containing hydrogen and carbon atoms, and may also contain heteroatoms such as oxygen, sulfur, nitrogen, and the like.

"Hydroprocessing" means a process wherein a hydrocarbonaceous product is contacted with hydrogen over a catalyst at pressures greater than atmospheric. Examples include hydrotreating, hydrocracking, hydroisomerization, and hydrodewaxing.

"Hydrotreated stream" means a hydrocarbonaceous stream that has been hydrotreated to remove impurities, such as elemental sulfur, nitrogen, or oxygen or compounds containing, sulfur, nitrogen, or oxygen. The hydrocarbonaceous stream may be a Fischer-Tropsch product stream or a convention petroleum product stream.

"Non-oxygenated hydrocarbon stream" refers to a hydrocarbonaceous product stream comprising less than approximately 10 ppm oxygen as oxygenates. For the specific example of a diesel with an average carbon number of about 12, 10 ppm oxygen as oxygenates corresponds to approximately 100 ppm oxygenates. The non-oxygenated hydrocarbon stream of the present invention may be isolated from a Fischer Tropsch product stream, may be a conventional petroleum product stream, or may be a hydrotreated stream.

"No detectable oxygenated species" means that any individual specific oxygenated species is below 1 ppm as oxygen.

"Substantially paraffinic product" refers to a product comprised of at least 50% paraffins.

"Syngas" is a mixture that includes hydrogen and carbon monoxide. In addition to these species, others may also be present, including, for example, water, carbon dioxide, unconverted light hydrocarbon feedstock, and various impurities.

"Oxygenate" means a compound that includes at least one oxygen atom. Oxygenates include for example, alcohols, ethers, carboxylic acids, and the like.

"Class of oxygenate species" means classes into which oxygenates may be separated. For example, alcohols, ethers, carboxylic acids, and esters are specific classes of oxygenated species.

"Integrated Process" means a process comprising a sequence of steps, some of which may be parallel to other steps in the process, but which are interrelated or somehow dependent upon either earlier or later steps in the total process.

DETAILED DESCRIPTION OF THE ILLUSTRATIVE EMBODIMENTS

Figure 1:
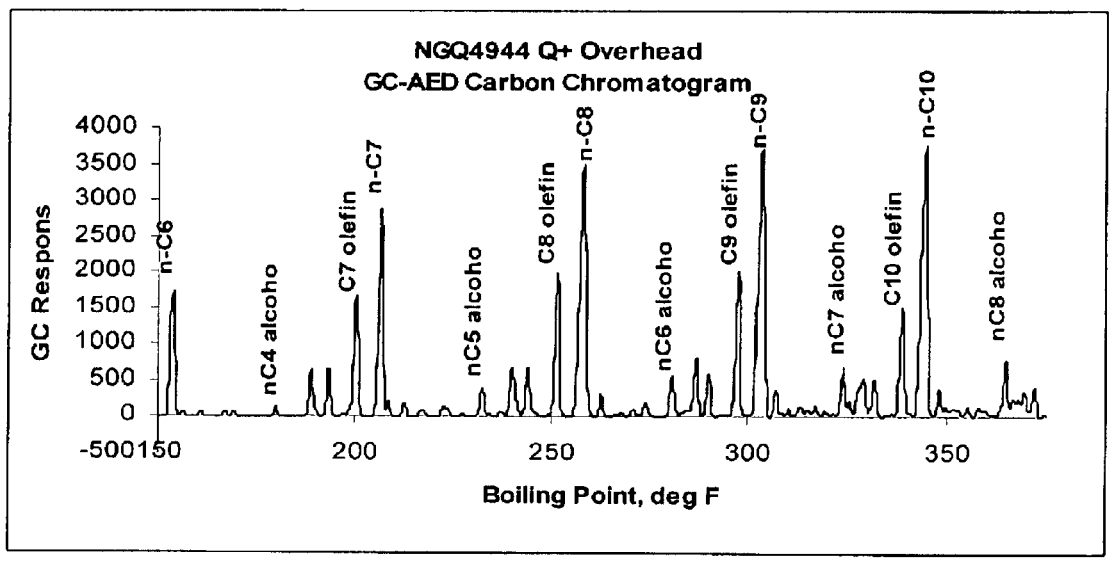
FIG. 1 illustrates a GC-AED analysis of the blended product of the example, showing alcohols and olefins.

The present invention provides processes that utilize the various products obtained or obtainable from a Fischer Tropsch reaction. The processes described herein provide Fischer Tropsch products that can be processed or blended to provide salable Fischer Tropsch products with desired oxygenate concentrations, and if required, desired oxygenate concentrations of specific individual oxygenates.

It has been discovered that GC-AED is an accurate analytical technique for measuring total oxygenate concentration and specific individual oxygenate compounds in hydrocarbon products from a Fischer Tropsch process. It is essential that the analytical method be sensitive enough to measure both the total oxygenate concentration and differentiate between specific individual oxygenates and thus provide measurements of the specific individual oxygenates. It has been discovered that in hydrocarbon products from a Fischer Tropsch process, GC-AED may be used to differentiate and measure individual oxygenates (e.g. primary alcohols) within a family of oxygenates (e.g. all alcohols), differentiate different families of oxygenates (e.g., alcohols and acids), and differentiate oxygenates by carbon number distribution. It has further been discovered that GC-AED allows for accurate and economical monitoring of very low levels of oxygenates, below the level of reliable detection by other analytical techniques, in hydrocarbon products from a Fischer Tropsch process. The oxygenate measurements obtained using GC-AED may be used to control various operations associated with producing Fischer Tropsch products to provide a product with a desired oxygenate concentration, and if required, a desired oxygenate concentration of specific individual oxygenates.

The basic GC-AED method according to the present invention comprises (i) introducing a mixture of the sample, an inert carrier gas therefor, and a reagent gas into an atomic emission spectrometer having plasma-excitation means; (ii) forming a plasma from said mixture, and (iii) detecting at least one oxygen or oxygen-related optical emission generated in the spectrometer. This method is as described in, for example, U.S. Pat. No. 5,151,371, the contents of which are hereby incorporated by reference in their entirety. A carbon-containing gas may be introduced in a controlled amount into the mixture that enters the plasma forming stage of step (ii) to enhance the selectivity for oxygen detection. In preferred embodiments, the carbon-containing gas may be introduced with the basic reagent gas and may replace a portion of the reagent gas on a v/v basis. The reagent gas, as modified by the introduction of the carbon-containing gas, may comprise nitrogen, hydrogen, or mixtures thereof and up to approximately 20 volume % of methane, propane, propylene, or n-butane. In a preferred method of conducting GC-AED according to the present invention, the inert carrier gas may be approximately 10% methane in nitrogen. According to the present invention, standard spectrometers for GC-AED may be used to monitor oxygenate concentrations.

In order to attain desired characteristics in a Fischer-Tropsch product, a desired concentration of oxygenated species in a substantially paraffinic Fischer-Tropsch product may be selected. A desired carbon number distribution and class of oxygenated species may also be selected. As one of skill in the art would readily understand, the concentration, carbon number distribution, and class of oxygenated species will be selected based on the end-use planned for the Fischer Tropsch product and the desired characteristics of the Fischer Tropsch product. The selected concentration of oxygenates may be achieved by purifying the Fischer Tropsch product to remove at least a portion of the oxygenates. The selected carbon number distribution may be achieved by purifying the Fischer Tropsch product to remove oxygenates that are smaller or larger than the selected carbon number. The selected class of oxygenates may be achieved by selectively purifying the Fischer Tropsch product such that undesired classes of oxygenates (i.e., acids) are removed and desired classes of oxygenates (i.e. alcohols) are retained.

By way of example, a Fischer Tropsch product containing no detectable oxygenate species may be desired. Accordingly, it may be desirable to remove substantially all oxygenated compounds from the Fischer-Tropsch products so that a Fischer Tropsch product containing no detectable oxygenated species is provided. A Fischer Tropsch product containing no detectable oxygenated species may be desired because oxygenates may interfere with subsequent processing operations by destroying catalysts. In addition, oxygenates may contribute to poor combustion properties. By way of example, it may be desirable to provide a Fischer Tropsch product containing no detectable oxygenated species to increase yields of high octane gasoline and diesel fuel. Furthermore, it may be desirable to remove oxygenates, in particular acids, to prevent damage to zeolite catalysts used in processing Fischer Tropsch products to provide salable products. It may be noted that, in the process of isomerizing the paraffins to make pumpable syncrude, oxygenates present in the isomerization feed may be removed. However, oxygenates may have an adverse effect on the performance of hydroisomerization and hydrocracking catalysts. Therefore, it may be desirable to remove oxygentates before hydroisomerization if the oxygente levels are high enough to potentially adversely affect the catalyst.

In the alternative, a Fischer Tropsch product containing oxygenate species may be desired. It may be desirable to have a selected concentration of oxygenates in a Fischer Tropsch product since oxygenates may provide beneficial properties. It may also be desirable to have a selected concentration of a specific class of oxygenates, for example alcohols not acids, or a specific carbon number distribution, for example, $C_7$–$C_{12}$ alcohols. The selected concentration of oxygenates may be achieved by purifying the Fischer Tropsch product to remove at least a portion of the oxygenates or by blending an oxygenate-rich Fischer Tropsch stream with a non-oxygenate containing hydrocarbonaceous stream, preferably a non-oxygenate containing Fischer Tropsch stream. The concentration of oxygenates, in particular individual oxygenates, will be selected based on the beneficial properties to be provided by the oxygenates and the end-use planned for the Fischer Tropsch product.

By way of example, if the Fischer Tropsch product is to be used as a diesel fuel additive, it may be desirable to contain a selected concentration of oxygenates, preferably a selected concentration of specific individual oxygenate compounds, so that the diesel fuel additive will reduce emissions when burned. Similarly, a Fischer Tropsch diesel fuel with an alcohol content between 500 and 5000 wppm may be a low emissions diesel fuel; therefore, it may be desirable to provide a Fischer Tropsch diesel fuel with an alcohol concentration in this range. Furthermore, if the Fischer Tropsch product is to be used as a jet fuel, it may be desirable to contain a selected concentration of oxygenates to improve the lubricity of the jet fuel. To improve the lubricity of the jet fuel, it is preferred to incorporate alcohols. Moreover, the valuable alcohols for improving lubricity are $C_{7+}$ alcohols, preferably $C_7$–$C_{12}$ alcohols, and more preferably $C_9$–$C_{12}$ primary alcohols. To improve lubricity, acids may also be useful, but at low levels. It has been discovered that GC-AED provides an analytical technique sensitive enough to differentiate and monitor the preferred alcohols in hydrocarbon products from a Fischer Tropsch process. In addition, if the Fischer Tropsch product is to be used as a diesel fuel, it may be desirable to contain a selected concentration of oxygenates, in particular oxygen-containing glycerol monoesters, to improve lubricity. Accordingly, to achieve beneficial properties provided by oxygenates, it may be necessary to select not only the concentration of the total oxygenates, but also the concentration of specific types of individual oxygenates.

GC-AED may be used to accurately and economically measure oxygenate concentration and specific individual oxygenate compounds at very low levels in products from a Fischer Tropsch process. With these oxygenate measurements, processes used to produce, upgrade, or finish the Fischer Tropsch products may be controlled such that the products provided have a desired oxygenate concentration, and if required, a desired oxygenate concentration of specific individual oxygenates (i.e. a desired carbon number distribution of oxygenated species or a desired class of oxygenated species). Accordingly, GC-AED may be used in conjunction with a Fischer Tropsch process to provide a Fischer Tropsch product with a desired oxygenate concentration, and if required, a desired oxygenate concentration of specific individual oxygenates.

In a Fischer-Tropsch synthesis process, liquid and gaseous hydrocarbons are formed by contacting a synthesis gas (syngas) comprising a mixture of hydrogen and carbon monoxide with a Fischer-Tropsch catalyst under suitable temperature and pressure reactive conditions. An advantage of using products prepared from the Fischer-Tropsch process is that they do not contain nitrogen and sulfur and generally do not contain aromatic compounds. Accordingly, they have minimal health and environmental impact. Fischer-Tropsch derived fuels, including for example, diesel fuels, are considered "green fuels" and are desirable as environmentally friendly.

Catalysts and conditions for performing Fischer-Tropsch synthesis are well known to those of skill in the art, and are described, for example, in EP 0 921 184 A1, the contents of which are hereby incorporated by reference in their entirety. In the Fischer-Tropsch synthesis process, synthesis gas (syngas) is converted to liquid hydrocarbons by contact with a Fischer-Tropsch catalyst under reactive conditions. Typically, methane and optionally heavier hydrocarbons (ethane and heavier) can be sent through a conventional syngas generator to provide synthesis gas. Generally, synthesis gas contains hydrogen and carbon monoxide, and may include minor amounts of carbon dioxide and/or water. The presence of sulfur, nitrogen, halogen, selenium, phosphorus and arsenic contaminants in the syngas is undesirable. For this reason, and depending on the quality of the syngas, it is preferred to remove sulfur and other contaminants from the feed before performing the Fischer Tropsch chemistry. Means for removing these contaminants are well known to those of skill in the art. For example, ZnO guard beds are preferred for removing sulfur impurities. Means for removing other contaminants are well known to those of skill in the art. It also may be desirable to purify the syngas prior to the Fischer Tropsch reactor to remove carbon dioxide produced during the syngas reaction and any additional sulfur compounds not already removed. This can be accomplished, for example, by contacting the syngas with a mildly alkaline solution (e.g., aqueous potassium carbonate) in a packed column.

In the Fischer Tropsch process, liquid and gaseous hydrocarbons are formed by contacting a synthesis gas comprising a mixture of $H_2$ and CO with a Fischer Tropsch catalyst under suitable temperature and pressure reactive conditions. The Fischer Tropsch reaction is typically conducted at temperatures of about 300 to 700° F. (149 to 371° C.), preferably about from 400 to 550° F. (204 to 228° C); pressures of about from 10 to 600 psia, (0.7 to 41 bars), preferably 30 to 300 psia, (2 to 21 bars) and catalyst space velocities of from about 100 to about 10,000 cc/g/hr., preferably 300 to 3,000 cc/g/hr.

Examples of conditions for performing Fischer-Tropsch type reactions are well known to those of skill in the art. Suitable conditions are described, for example, in U.S. Pat. Nos. 4,704,487, 4,507,517, 4,599,474, 4,704,493, 4,709,108, 4,734,537, 4,814,533, 4,814,534 and 4,814,538, the contents of each of which are hereby incorporated by reference in their entirety.

The products of the Fischer Tropsch synthesis process may range from $C_1$ to $C_{200+}$ with a majority in the $C_5$ to $C_{100+}$ range, and the products may be distributed in one or more product fractions. The reaction can be conducted in a variety of reactor types, for example, fixed bed reactors containing one or more catalyst beds, slurry reactors, fluidized bed reactors, or a combination of different type reactors. Such reaction processes and reactors are well known and documented in the literature.

Slurry Fischer-Tropsch processes, which is a preferred process in the practice of the invention, utilize superior heat (and mass) transfer characteristics for the strongly exothermic synthesis reaction and are able to produce relatively high molecular weight, paraffinic hydrocarbons when using a cobalt catalyst. In a slurry process, a syngas comprising a mixture of $H_2$ and CO is bubbled up as a third phase through a slurry in a reactor which comprises a particulate Fischer-Tropsch type hydrocarbon synthesis catalyst dispersed and suspended in a slurry liquid comprising hydrocarbon products of the synthesis reaction which are liquid at the reaction conditions. The mole ratio of the hydrogen to the carbon monoxide may broadly range from about 0.5 to 4, but is more typically within the range of from about 0.7 to 2.75 and preferably from about 0.7 to 2.5. A particularly preferred Fischer-Tropsch process is taught in EP 0609079, herein incorporated by reference in its entirety.

The products from Fischer-Tropsch reactions performed in slurry bed reactors generally include a light reaction product and a waxy reaction product. The light reaction product (i.e. the condensate fraction) includes hydrocarbons boiling below about 700° F. (e.g., tail gases through middle distillates), largely in the $C_5$–$C_{20}$ range, with decreasing amounts up to about $C_{30}$. The waxy reaction product (i.e., the wax fraction) includes hydrocarbons boiling above 600° F. (e.g., vacuum gas oil through heavy paraffins), largely in the $C_{20}$+ range, with decreasing amounts down to $C_{10}$. Both the light reaction product and the waxy product are substantially paraffinic. The waxy product generally comprises greater than 70% normal paraffins, and often greater than 80% normal paraffins. The light reaction product comprises paraffinic products with a significant proportion of alcohols and olefins. In some cases, the light reaction product may comprise as much as 50%, and even higher, alcohols and olefins.

The product from the Fischer-Tropsch process may be further processed using, for example, hydrocracking, hydroisomerization, and hydrotreating. Such processes crack the larger synthesized molecules into fuel range and lube range molecules with more desirable boiling points, pour points, and viscosity index properties. Such processes may also saturate oxygenates and olefins to meet the particular needs of a refinery. These processes are well known to those of skill in the art.

In general, suitable Fischer-Tropsch catalysts comprise one or more Group VIII catalytic metals such as Fe, Ni, Co, Ru and Re. Additionally, a suitable catalyst may contain a promoter. Thus, a preferred Fischer-Tropsch catalyst comprises effective amounts of cobalt and one or more of Re, Ru, Pt, Fe, Ni, Th, Zr, Hf, U, Mg and La on a suitable inorganic support material, preferably one which comprises one or more refractory metal oxides. In general, the amount of cobalt present in the catalyst is between about 1 and about 50 weight percent of the total catalyst composition. The catalysts can also contain basic oxide promoters such as $ThO_2$, $La_2O_3$, MgO, and $TiO_2$, promoters such as $ZrO_2$, noble metals (Pt, Pd, Ru, Rh, Os, Ir), coinage metals (Cu, Ag, Au), and other transition metals such as Fe, Mn, Ni, and Re. Support materials including alumina, silica, magnesia and titania or mixtures thereof may be used. Preferred supports for cobalt containing catalysts comprise titania. Useful catalysts and their preparation are known to those of skill in the art.

Certain catalysts are known to provide chain growth probabilities that are relatively low to moderate, for example, iron-containing catalysts, and the reaction products include a relatively high proportion of low molecular ($C_{2-8}$) weight olefins and a relatively low proportion of high molecular weight ($C_{30}$+) waxes. Certain other catalysts are known to provide relatively high chain growth probabilities, for example, cobalt-containing catalysts, and the reaction products include a relatively low proportion of low molecular ($C_{2-8}$) weight olefins and a relatively high proportion of high molecular weight ($C_{30}$+) waxes. Such catalysts are well known to those of skill in the art and can be readily obtained and/or prepared. The preferred catalysts of this invention contain either Fe or Co, with Co being preferred.

Fischer-Tropsch derived products include, for example, Fischer-Tropsch naphtha, Fischer-Tropsch jet fuel, Fischer-Tropsch diesel fuel, Fischer-Tropsch solvent, Fischer-Tropsch lube base stock, Fischer-Tropsch lube base oil, and mixtures thereof. Distillate fuels derived from the Fischer-Tropsch process have excellent burning properties. Fischer-Tropsch products contain essentially no aromatics or heteroatoms.

A Fischer Tropsch product stream containing oxygenated species may be isolated from a Fischer-Tropsch product stream in a variety of ways. A Fischer Tropsch product stream containing oxygenates may be isolated by, for example, simple distillation, fractional distillation, extraction, adsorption, membrane processes, and the like. In the Fischer Tropsch process, the desired Fischer Tropsch product typically will be isolated by distillation. If higher boiling products, with boiling points above 700° F., are to be separated by distillation, operation at sub-atmospheric pressures are used. Crystallization and filtration are used to isolate waxy compounds from non-waxy compounds. The crystallization is done by mixing the product with a solvent (typically a mixture of a ketone, for example, methyl-ethyl-ketone, and an aromatic, for example, toluene). The mixture is chilled forming wax crystals which are separated by rotary drum filters. This is the typical process used to prepare lubricating oils and waxes from petroleum stocks.

The isolated Fischer Tropsch product stream containing oxygenates may be purified, or have its oxygenate content controlled by, any of several operations associated with the downstream processing of Fischer Tropsch products. Accordingly, a selected concentration of oxygenates for the Fischer Tropsch product may be achieved by purifying the Fischer Tropsch product to remove at least a portion of the oxygenates or by blending an oxygenate-rich Fischer Tropsch stream with a non-oxygenate containing hydrocarbonaceous stream. The non-oxygenate containing hydrocarbonaceous stream may be a conventional petroleum product, a non-oxygenate containing Fischer Tropsch stream, or a hydrotreated stream. In addition, a selected carbon number distribution of oxygenates or specific class of oxygenated species for the Fischer Tropsch product may be achieved by selectively purifying the Fischer Tropsch product or by blending an oxygenate-rich Fischer Tropsch stream.

The purification processes typically will be used to remove at least a portion of the oxygenated species or may be used to provide a Fischer Tropsch product comprising no detectable oxygenated species, as desired. In the methods of the present invention, GC-AED is used to monitor the oxygenate concentration, and optionally the carbon number distribution and class of oxygenates, of the Fischer Tropsch product stream containing oxygenates to be purified or to be blended. GC-AED is also used to monitor the oxygenate concentration, and optionally the carbon number distribution and class of oxygenates, of the resulting purified or blended product stream.

By way of example, the purification processes may include processes used to produce, upgrade, finish, or convert the Fischer Tropsch products to provide salable products. The purification processes may include extraction, such as washing the effluent from a Fischer Tropsch process with water to remove oxygenates. Lighter alcohols such as methanol may also be used in extraction processes. Furthermore, the purification processes may include hydroprocessing the Fischer Tropsch products. Hydroprocessing includes hydrotreating, hydrocracking, and hydroisomerization processes. Moreover, the purification processes may include adsorption. For example, a Fischer Tropsch product containing oxygenates may be contacted with or passed over or through an absorbent or absorbent bed selective for oxygenates. Absorbents selective for oxygenates include, for example, zeolites which remove oxygenates by size exclusion and/or polarity.

Hydrotreating may be used to reduce the total oxygenate content, and specifically to reduce the acid content. Typical hydrotreating conditions include a reaction temperature between 400° F.–900° F. (204° C.–482° C.), preferably 650° F-850° F. (343° C.–454° C.); a pressure between 500 to 5000 psig (pounds per square inch gauge) (3.5–34.6 MPa), preferably 1000 to 3000 psig (7.0–20.8 MPa); a feed rate (LHSV or liquid hourly space velocity) of 0.5 $hr^{-1}$ to 20 $hr^{-1}$ (v/v);

and overall hydrogen consumption 300 to 2000 scf (standard cubic foot) per barrel of liquid hydrocarbon feed (53.4–356 m$^3$ H$_2$/m$^3$ feed). The hydrotreating catalyst for the beds will typically be a composite of a Group VI metal or compound thereof, and a Group VIII metal or compound thereof supported on a porous refractory base such as alumina. Examples of hydrotreating catalysts are alumina supported cobalt-molybdenum, nickel sulfide, nickel-tungsten, cobalt-tungsten and nickel-molybdenum. Typically such hydrotreating catalysts are presulfided.

Hydrocracking is another example of hydroprocessing. Typical hydrocracking conditions include a reaction temperature, 400° F.–950° F. (204° C.–510° C.), preferably 650° F.–850° F. (343° C.–454° C.); reaction pressure 500 to 5000 psig (3.5–34.5 MPa), preferably 1500–3500 psig (10.4–24.2 MPa); LHSV, 0.1 to 15 hr$^{-1}$ (v/v), preferably 0.25–2.5 hr$^{-1}$; and hydrogen consumption 500 to 2500 scf per barrel of liquid hydrocarbon feed (89.1–445 m$^3$ H2/m$^3$ feed). The hydrocracking catalyst generally comprises a cracking component, a hydrogenation component and a binder. Such catalysts are well known in the art. The cracking component may include an amorphous silica/alumina phase and/or a zeolite, such as a Y-type or USY zeolite. The binder is generally silica or alumina. The hydrogenation component will be a Group VI, Group VII, or Group VIII metal or oxides or sulfides thereof, preferably one or more of molybdenum, tungsten, cobalt, or nickel, or the sulfides or oxides thereof. If present in the catalyst, these hydrogenation components generally make up from about 5% to about 40% by weight of the catalyst. Alternatively, platinum group metals, especially platinum and/or palladium, may be present as the hydrogenation component, either alone or in combination with the base metal hydrogenation components molybdenum, tungsten, cobalt, or nickel. If present, the platinum group metals will generally make up from about 0.1% to about 2% by weight of the catalyst.

Hydroisomerization is another example of hydroprocessing. Typical hydroisomerization conditions are well known in the literature and can vary widely. Hydroisomerization processes are typically carried out at a temperature between 200° F. and 700° F., preferably 300° F. to 650° F., with a LHSV between 0.1 and 10, preferably between 0.25 and 5. Hydrogen is employed such that the mole ratio of hydrogen to hydrocarbon is between 1:1 and 15:1. Catalysts useful for hydroisomerization processes are generally bifunctional catalysts that include a dehydrogenation/hydrogenation component and an acidic component. The acidic component may include one or more of amorphous oxides such as alumina, silica or silica-alumina; a zeolitic material such as zeolite Y, ultrastable Y, SSZ-32, Beta zeolite, mordenite, ZSM-5 and the like, or a non-zeolitic molecular sieve such as SAPO-11, SAPO-31 and SZPO-41. The acidic component may further include a halogen component, such as fluorine. The hydrogenation component may be selected from the Group VIII noble metals such as platinum and/or palladium, from the Group III non-noble metals such as nickel and tungsten, and from the Group VI metals such as cobalt and molybdenum. If present, the platinum group metals will generally make up from about 0.1% to about 2% by weight of the catalyst. If present in the catalyst, he non-noble metal hydrogenation components generally make up from about 5% to about 40% by weight of the catalyst.

To control the oxygenate concentrations, Fischer Tropsch product streams containing oxygenates may also be blended with at least one non-oxygenate containing hydrocarbon stream. The non-oxygenate containing hydrocarbonaceous stream may be a conventional petroleum product, a non-oxygenate containing Fischer Tropsch stream, or a hydrotreated stream. Methods for blending the Fischer Tropsch product stream containing oxygenated species with at least one non-oxygenate containing hydrocarbon stream and controlling the quantity of individual streams added to form the blended stream would be readily understood and devised by one of skill in the art. As one of skill in the art would readily understand and be able to devise, these streams may be blended in a variety of ways to achieve the selected oxygenate concentration. The streams may be blended in a blending zone and one blended Fischer Tropsch product may be provided from the blending zone. The relative feed rates to the blending zone may also be controlled to generate the desired oxygenate concentration. By way of example, if a higher oxygenate concentration was selected, a larger quantity of stream from the Fischer Tropsch product stream containing oxygenated species may be blended and in the alternative, if a lower oxygenate concentration was selected, a larger quantity of non-oxygenate containing hydrocarbon stream may be blended.

As described above, GC-AED is used to monitor the oxygenate concentration, and optionally the carbon number distribution and class of oxygenates, of the Fischer Tropsch product stream containing oxygenates to be purified or blended and of the resulting purified or blended product stream. The GC-AED analysis may be performed also as described above. The data obtained from the GC-AED analysis of the Fischer Tropsch product stream containing oxygenates to be purified or blended and of the resulting purified or blended product stream may be used to monitor and control the purification process or the blending process.

Accordingly, the data obtained from the GC-AED may be used in controlling the purification process or the blending process. The method of control, however, will depend on the specific operation used. By way of example, the purification process of extraction may be controlled and adjusted in accordance with the data obtained from the GC-AED by any one of the following processes: adjusting the amount of solvent added to the substantially paraffinic product stream, adjusting contacting time between the solvent and the substantially paraffinic product stream, adjusting contacting efficiency between the solvent and the substantially paraffinic product stream, adjusting the temperature of the solvent, and combinations thereof. By way of example, the following extraction process conditions may be increased if the GC-AED data indicates that oxygenate level is higher than the selected concentration: increasing the amount of solvent added to the substantially paraffinic product stream, increasing the contacting time between the solvent and the substantially paraffinic product stream, increasing the contacting efficiency between the solvent and the substantially paraffinic product stream, increasing mixing energy such as by a stirrer or pump, increasing the temperature of the solvent, and combinations thereof. In the alternative, the above-listed process conditions may be decreased if the GC-AED data indicates that oxygenate level is lower than the selected concentration.

Also by way of example, the purification process of hydrotreating may be controlled and adjusted in accordance with the data obtained from the GC-AED by any one of the following processes: adjusting the catalyst temperature, regenerating the catalyst, changing the catalyst, adjusting the liquid hourly space velocity (LHSV) of the substantially paraffinic product stream passed over the catalyst, and adjusting the pressure in the hydrotreating unit could all be used to control oxygenate content. By way of example, the following hydrotreating process conditions may be adjusted if the GC-AED data indicates that oxygenate level is higher than the selected concentration: increasing the catalyst temperature, regenerating the catalyst, changing the catalyst, decreasing the LHSV of the substantially paraffinic product stream passed over the catalyst, increasing the pressure in the hydrotreating, and combinations thereof. In the alternative, the above-listed process conditions may be adjusted conversely if the GC-AED data indicates that oxygenate level is lower than the selected concentration.

Further by way of example, the adsorption process may be controlled and adjusted in accordance with the data obtained from the GC-AED by any one of the following processes: regenerating the adsorbent, changing the adsorbent, and adjusting the LHSV of the substantially paraffinic product stream passed over the adsorbent. By way of example, the following adsorption process conditions may be adjusted if the GC-AED data indicates that oxygenate level is higher than the selected concentration: regenerating the catalyst, changing the catalyst, decreasing the LHSV of the substantially paraffinic product stream passed over the catalyst, and combinations thereof. In the alternative, the above-listed process conditions may be adjusted conversely if the GC-AED data indicates that oxygenate level is lower than the selected concentration.

Moreover, for blending a Fischer Tropsch product stream containing oxygenated species with a non-oxygenate containing hydrocarbon stream, the data obtained from the GC-AED analysis may be used to adjust and control the blending. By way of example, if the GC-AED data indicates that the oxygenate level is lower than the selected concentration, a larger quantity of the Fischer Tropsch product stream containing oxygenated species may be blended. In the alternative, if the GC-AED data indicates that the oxygenate level is higher than the selected concentration, a larger quantity of non-oxygenate containing hydrocarbon stream may be blended. Accordingly, the ratio of the two streams to be blended may be adjusted in accordance with the GC-AED data to achieve a blend product with the selected oxygenate concentration.

The oxygenate measurements obtained using GC-AED may be used to control various operations associated with producing Fischer Tropsch products to provide a product with a desired oxygenate concentration, and if required, a desired oxygenate concentration of specific individual oxygenates. The data obtained from the GC-AED analysis may be used in a process to produce a substantially paraffinic Fischer-Tropsch product comprising a selected oxygenate concentration in which the selected oxygenate concentration is achieved by purifying a Fischer Tropsch product stream to remove a portion of the oxygenated species. The data may also be used to produce a substantially paraffinic Fischer-Tropsch product comprising a selected oxygenate carbon number distribution in which the selected oxygenate carbon number distribution is achieved by purifying the Fischer Tropsch product stream to remove a portion of the oxygenated species. The data may further be used to produce a substantially paraffinic Fischer-Tropsch product comprising a selected class of oxygenated species in which the selected class of oxygenated species is achieved by purifying the Fischer Tropsch product stream to remove a portion of the oxygenated species. In addition, the data obtained from the GC-AED analysis may be used in a process to produce a substantially paraffinic Fischer-Tropsch product comprising a no detectable oxygenates in oxygenates are removed below a detectable level by purifying a Fischer Tropsch product stream to remove oxygenated species.

Furthermore, the data obtained from the GC-AED analysis may be used in a process to produce a blended Fischer Tropsch product comprising a selected oxygenate concentration in which the selected oxygenate concentration is achieved by blending a Fischer Tropsch product stream containing oxygenates with at least one non-oxygenate containing hydrocarbon stream. The data may also be used to produce a blended Fischer-Tropsch product comprising a selected oxygenate carbon number distribution in which the selected oxygenate carbon number distribution is achieved by blending a Fischer Tropsch product stream containing oxygenates with at least one non-oxygenate containing hydrocarbon stream. The data may further be used to produce a blended Fischer-Tropsch product comprising a selected class of oxygenated species in which the selected class of oxygenated species is achieved by blending a Fischer Tropsch product stream containing oxygenates with at least one non-oxygenate containing hydrocarbon stream.

Moreover, the data obtained from the GC-AED analysis may be used in an integrated process to produce a blended Fischer Tropsch product. In the integrated process a Fischer Tropsch product comprising a selected oxygenate concentration is produced by purifying a Fischer Tropsch product stream to remove a portion of the oxygenated species. This Fischer Tropsch product stream comprising a selected oxygenate concentration is then blended with at least one non-oxygenate containing hydrocarbon stream. The blended product has a selected oxygenate concentration. The blended product may also have a selected carbon number distribution or a selected class of oxygenated species.

Products produced according to the methods of the present invention include, but are not limited to, pumpable syncrudes, diesel fuel additives, diesel fuels with reduced emissions, jet fuels with improved lubricity, and the like. The products may further comprise additives, including, for example, dispersants, detergents, anti-oxidants, antimicrobials, ignition improvers, and the like.

EXAMPLES

The invention will be further explained by the following illustrative examples that are intended to be non-limiting.

In this study an oxygenate-containing light condensate was blended with a de-oxygenated condensate containing heavier wax, both derived from a Fischer-Tropsch process. The de-oxygenated condensate containing heavier wax had previously been hydrotreated to remove the oxygenates. Properties of the streams were as follows:

|  | Condensate | Wax | Blend |
|---|---|---|---|
| API Gravity, ° | 57.5 | 40.5 | 51.1 |
| Oxygen by Neutron Activation Analysis, weight % | 1.41 | 0.009 |  |
| Karl Fischer Water, ppm | 775 | 45 |  |
| 0.5/5 | 96/202 | 675/699 | 86/201 |
| 10/30 | 211/307 | 712/754 | 255/384 |
| 50/ | 385/ | 802/ | 504/ |
| 70/90 | 454/531 | 871/980 | 585/656 |
| 95/99 | 575/670 | 1018/1096 | 673/692 |

Figure 2:
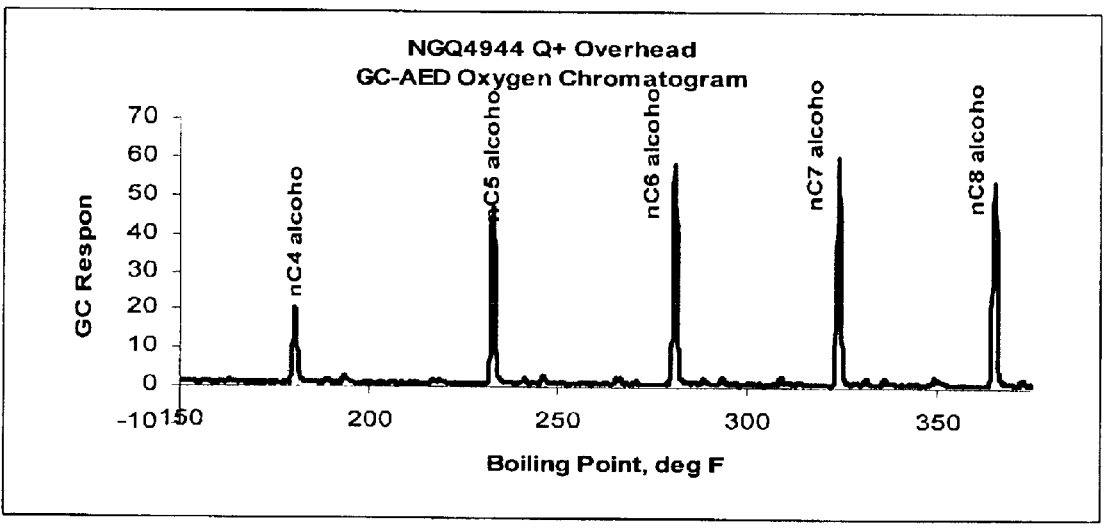
FIG. 2 illustrates a GC-AED analysis of the blended product of the example, showing alcohols.

FIG. 1 is the GC-AED analysis of the blended product of the example, showing alcohols and olefins, and FIG. 2 is the GC-AED analysis of the blended product of the example, showing only alcohols.

This data shows the utility of GC-AED in monitoring and controlling the blending of oxygenate-containing streams.

The blend was hydrotreated over a typical commercial Ni—Mo catalyst at the following conditions:

| | |
|---|---|
| Total Pressure, psig | 1000 |
| LHSV, hr$^{-1}$ | 5.0, 10.0, 15.0 |
| Catalyst Temperature, °F. | 650 and 700 |
| Once-through H$_2$ rate | 6500 SCFB (standard cubic feet per barrel). |

Under all conditions (except the mildest), the oxygenate content was reduced to below the level of detection by GC-AED.

| Run, Hours | Catalyst Temperature, °F. | LHSV, hr$^{-1}$ | Total Pressure, psig | H$_2$ Rate, SCFB | Olefins | Oxygenates |
|---|---|---|---|---|---|---|
| 208 | 700 | 5.17 | 1000 | 6149 | None | None |
| 256 | 700 | 9.92 | 1000 | 6407 | None | None |
| 383 | 700 | 14.96 | 1000 | 5963 | None | None |
| 496 | 648 | 4.97 | 1000 | 6400 | None | None |
| 529 | 648 | 14.55 | 1000 | 6123 | None | None |
| 592 | 547 | 5.10 | 1000 | 6237 | None | None |
| 688 | 446 | 5.05 | 1000 | 6298 | None | None |
| 736 | 347 | 4.95 | 1000 | 6429 | Detected | Detected |

Figure 3:
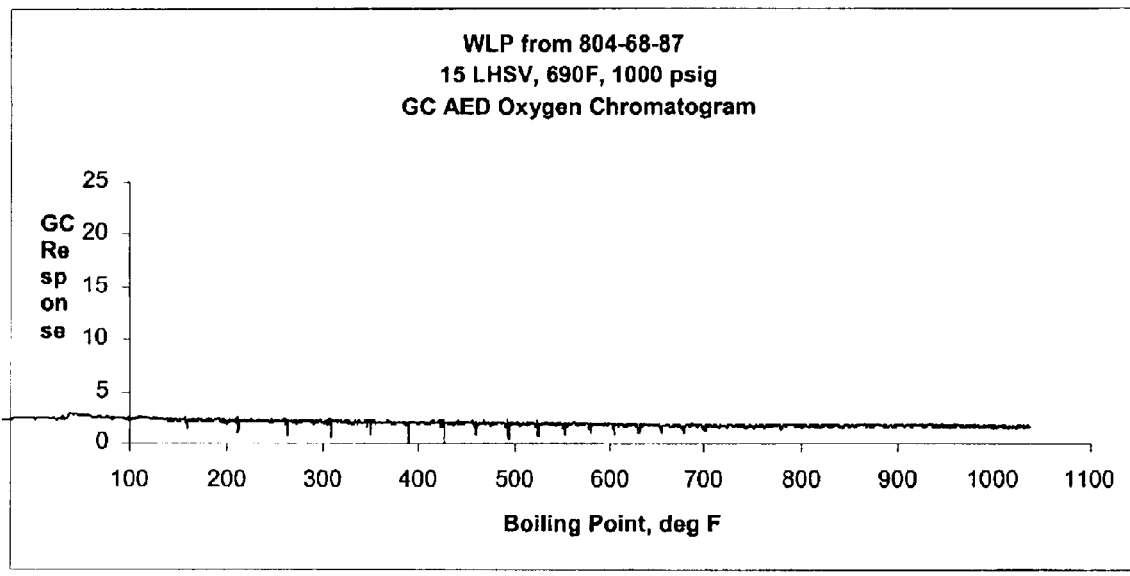
FIG. 3 illustrates a GC-AED analysis of the blended product of the example following hydrotreatment over a typical commercial Ni—Mo catalyst, showing no detectable oxygenates.
Figure 4:
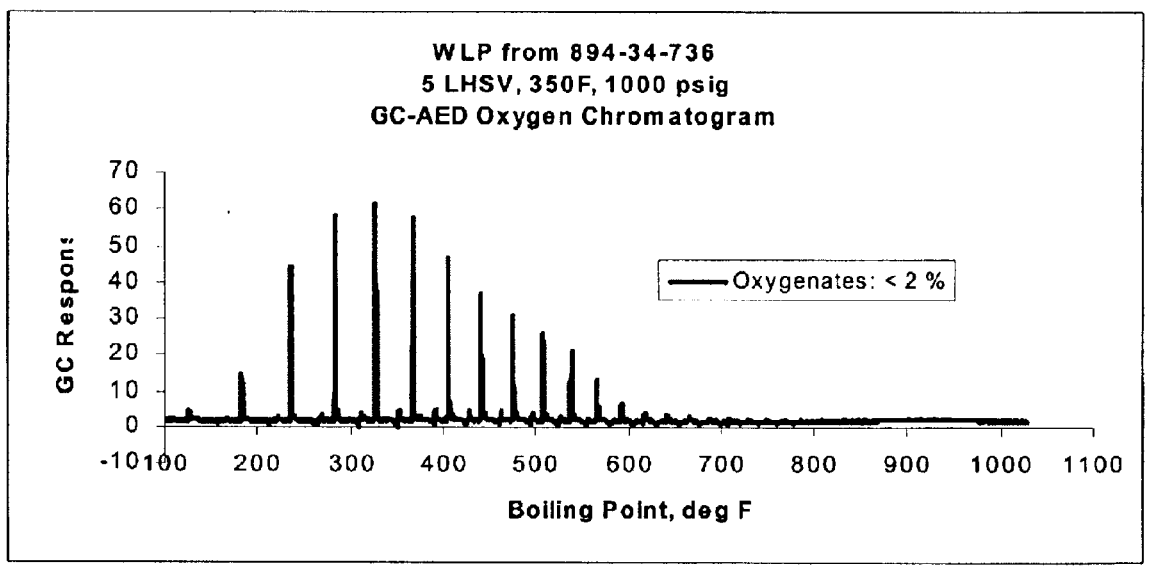
FIG. 4 illustrates a GC-AED analysis of the blended product of the example following the mildest hydrotreating operation, showing very low levels of oxygenates with which accurate resolution of individual species is possible.

FIG. 3 is the GC-AED analysis of the blended product of the example following hydrotreatment over a typical commercial Ni—Mo catalyst, showing no detectable oxygenates, and FIG. 4 is the GC-AED analysis of the blended product of the example following the mildest hydrotreating operation, showing very low levels of oxygenates with which accurate resolution of individual species is possible.

Various modifications and alterations of this invention will become apparent to those skilled in the art without departing from the scope and spirit of this invention. Other objects and advantages will become apparent to those skilled in the art from a review of the preceding description.

What is claimed is:

1. A method for producing a substantially paraffinic Fischer-Tropsch product comprising at least one oxygenated species, the method comprising the steps of:
    (a) selecting a concentration of oxygenated species in the substantially paraffinic Fischer-Tropsch product;
    (b) performing a Fischer-Tropsch synthesis to provide a Fischer-Tropsch product stream;
    (c) isolating a substantially paraffinic product stream comprising oxygenated species from the Fischer-Tropsch product stream;
    (d) purifying the substantially paraffinic product stream to remove a portion of oxygenated species to provide a substantially paraffinic Fischer-Tropsch product comprising at least one oxygenated species;
    (e) monitoring the substantially paraffinic Fischer-Tropsch product for concentration of oxygenated species by GC-AED; and
    (f) adjusting the conditions of the purification of step (d) to ensure that the concentration of the oxygenated species in the substantially paraffinic Fischer-Tropsch product complies with the selected concentration.

2. The method of claim 1, further comprising selecting a carbon number distribution of oxygenated species, monitoring the substantially paraffinic Fischer-Tropsch product for the carbon number distribution of oxygenated species by GC-AED, and adjusting the conditions of the purification of step (d) to ensure that the carbon number distribution of oxygenated species in the substantially paraffinic Fischer-Tropsch product complies with the selected carbon number distribution.

3. The method of claim 1, further comprising selecting a specific class of oxygenated species, monitoring the substantially paraffinic Fischer-Tropsch product for the class of oxygenated species by GC-AED, and adjusting the conditions of the purification of step (d) to ensure that the class of oxygenated species in the substantially paraffinic Fischer-Tropsch product complies with the selected class.

4. The method of claim 3, wherein the specific class of oxygenated species is alcohols.

5. The method of claim 1, wherein the substantially paraffinic product stream of step (c) is isolated from the Fischer-Tropsch product stream by distillation.

6. The method of claim 1, wherein the purification of step (d) is performed by a process selected from the group consisting of hydrotreating, hydrocracking, adsorption, extraction and combinations thereof.

7. The method of claim 6, wherein the purification is performed by hydrotreating the substantially paraffinic product stream over a hydrotreating catalyst in a hydrotreating unit.

8. The method of claim 7, wherein the adjustment of step (f) is performed by a process selected from the group consisting of adjusting the catalyst temperature, regenerating the catalyst, changing the catalyst, adjusting the LHSV of the substantially paraffinic product stream passed over the catalyst, adjusting the pressure in the hydrotreating unit, and combinations thereof.

9. The method of claim 6, wherein the purification is performed by passing the substantially paraffinic product stream over an adsorbent.

10. The method of claim 9, wherein the adjustment of step (f) is performed by a process selected from the group consisting of regenerating the adsorbent, changing the adsorbent, adjusting the LHSV of the substantially paraffinic product stream passed over the adsorbent, and combinations thereof.

11. The method of claim 6, wherein the purification is performed by extraction by adding an amount of solvent to the substantially paraffinic product stream.

12. The method of claim 11 wherein the adjustment of step (f) is performed by a process selected from the group consisting of adjusting the amount of solvent added to the substantially paraffinic product stream, adjusting contacting time between the solvent and the substantially paraffinic product stream, adjusting contacting efficiency between the solvent and the substantially paraffinic product stream, adjusting the temperature of the solvent, and combinations thereof.

13. The method of claim 11 wherein the purification is performed by extraction with water.

14. The method of claim 1 wherein the substantially paraffinic Fischer-Tropsch product is a diesel fuel additive.

15. A method for preparing a blended Fischer-Tropsch product comprising at least one oxygenated species, the method comprising the steps of:
   (a) selecting a concentration of oxygenated species in the blended Fischer-Tropsch product;
   (b) performing a Fischer-Tropsch synthesis to provide a Fischer-Tropsch product stream;
   (c) isolating a substantially paraffinic product stream comprising oxygenated species from the Fischer-Tropsch product stream;
   (d) blending the substantially paraffinic product stream with at least one non-oxygenate containing hydrocarbon stream to provide a blended product comprising at least one oxygenated species;
   (e) monitoring the blended product for concentration of oxygenated species by GC-AED; and
   (f) adjusting the blending ratio of step (d) to ensure that the concentration of the oxygenated species in the blended product complies with the selected concentration.

16. The method of claim 15, further comprising selecting a carbon number distribution of oxygenated species, monitoring the substantially paraffinic Fischer-Tropsch product for the carbon number distribution of oxygenated species by GC-AED, and adjusting the conditions of the purification of step (d) to ensure that the carbon number distribution of oxygenated species in the substantially paraffinic Fischer-Tropsch product complies with the selected carbon number distribution.

17. The method of claim 15, further comprising selecting a specific class of oxygenated species, monitoring the substantially paraffinic Fischer-Tropsch product for class of oxygenated species by GC-AED, and adjusting the conditions of the purification of step (d) to ensure that the class of oxygenated species in the substantially paraffinic Fischer-Tropsch product complies with the selected class.

18. The method of claim 17, wherein the specific class of oxygenated species is alcohols.

19. The method of claim 15, wherein the substantially paraffinic product stream of step (c) is isolated from the Fischer-Tropsch product stream by distillation.

20. The method of claim 15, wherein the at least one non-oxygenate containing hydrocarbon stream is comprised of a non-oxygenate containing Fischer-Tropsch product stream and the method further comprises the step of isolating the non-oxygenate containing Fischer-Tropsch product stream from the Fischer-Tropsch product stream.

21. The method of claim 20, wherein the substantially paraffinic product stream of step (c) comprises at least one alcohol and wherein the blended product is a diesel fuel with reduced emissions.

22. The method of claim 15, wherein the at least one non-oxygenate containing hydrocarbon stream is a conventional petroleum product.

23. The method of claim 15, wherein the at least one non-oxygenate containing hydrocarbon stream is a hydrotreated stream and wherein the blended product is a pumpable syncrude.

24. The method of claim 15, wherein the concentration of oxygenated species is between 100 and 5000 wppm of oxygen on a water-free basis.

25. The method of claim 24, wherein the blended product is selected from the group consisting of diesel fuel and jet fuel.

26. The method of claim 25, further comprising the step of adding to the blended product an additive selected from the group consisting of dispersants, detergents, anti-oxidants and ignition improvers.

27. The method of claim 16, wherein the concentration of oxygenated species is selected to improve the lubricity of the blended Fischer-Tropsch product and $C_7$–$C_{12}$ is selected as the carbon number distribution.

28. The method of claim 17, wherein the concentration of oxygenated species is selected to improve the lubricity of the blended Fischer-Tropsch product and $C_7$–$C_{12}$ alcohols are selected as the class of oxygenated species.

29. The method of claim 28, wherein the blended Fischer Tropsch product is a jet fuel.

30. An integrated process for preparing a blended Fischer-Tropsch product comprising at least one oxygenated species, the method comprising the steps of:
   (a) producing a substantially paraffinic Fischer-Tropsch product comprising at least one oxygenated species, the method comprising the steps of:
      (i) selecting a concentration and carbon number distribution of oxygenated species in the substantially paraffinic Fischer-Tropsch product;
      (ii) performing a Fischer-Tropsch synthesis to provide a Fischer-Tropsch product stream;
      (iii) isolating a substantially paraffinic product stream comprising oxygenated species from the Fischer-Tropsch product stream;
      (iv) purifying the substantially paraffinic product stream in a purification process to remove a portion of oxygenated species to provide a substantially paraffinic Fischer-Tropsch product comprising at least one oxygenated species;
      (v) monitoring the substantially paraffinic Fischer-Tropsch product for concentration and carbon number distribution of oxygenated species by GC-AED; and
      (vi) adjusting the conditions of the purification of step (iv) to ensure that the concentration and carbon number distribution of the oxygenated species in the substantially paraffinic Fischer-Tropsch product comply with the selected concentration and carbon number distribution;
   (b) selecting a concentration and carbon number distribution of oxygenated species in the blended Fischer-Tropsch product;
   (c) blending the substantially paraffinic Fischer-Tropsch product with at least one non-oxygenate containing hydrocarbon stream to provide a blended product comprising at least one oxygenated species;
   (d) monitoring the blended product for concentration and carbon number distribution of oxygenated species by GC-AED; and
   (e) adjusting the blending ratio of step (d) to ensure that the concentration and carbon number distribution of the oxygenated species in the blended product comply with the selected concentration and carbon number distribution.

31. The method of claim 30, wherein the at least one non-oxygenate containing hydrocarbon stream is a conventional petroleum product.

32. The method of claim 30, wherein the at least one non-oxygenate containing hydrocarbon stream is a non-oxygenate containing Fischer-Tropsch product stream and the method further comprises the step of isolating the non-oxygenate containing Fischer-Tropsch product stream from the Fischer-Tropsch product stream.

33. A method for controlling a process for producing a substantially paraffinic Fischer-Tropsch product comprising no detectable oxygenated species, the method comprising the steps of:

(a) performing a Fischer-Tropsch synthesis to provide a Fischer-Tropsch product stream;

(b) isolating a substantially paraffinic product stream comprising oxygenated species from the Fischer-Tropsch product stream;

(c) purifying the substantially paraffinic product stream to remove oxygenated species to provide a substantially paraffinic Fischer-Tropsch product comprising no detectable oxygenated species;

(d) monitoring the substantially paraffinic Fischer-Tropsch product for concentration of oxygenated species by GC-AED; and (e) adjusting the conditions of the purification of step (c) to ensure that the concentration of the oxygenated species in the substantially paraffinic Fischer-Tropsch product is not detectable.

34. The method of claim 28 wherein the purification of step (c) is performed by a process selected from the group consisting of hydrotreating, hydrocracking, adsorption, extraction and combinations thereof.

35. The method of claim 34 wherein the purification is performed by hydrotreating the substantially paraffinic product stream over a hydrotreating catalyst in a hydrotreating unit.

36. The method of claim 35 wherein the adjustment of step (e) is performed by a process selected from the group consisting of adjusting the catalyst temperature, regenerating the catalyst, changing the catalyst, adjusting the LHSV of the substantially paraffinic product stream passed over the catalyst, adjusting the pressure in the hydrotreating unit, and combinations thereof.

37. The method of claim 3, wherein the isolated substantially paraffinic product stream of (c) contains alcohols and acids and the substantially paraffinic product stream is selectively purified to remove the acids and retain the alcohols.

* * * * *